(12) United States Patent
Dreyfuss

(10) Patent No.: US 8,348,975 B2
(45) Date of Patent: Jan. 8, 2013

(54) METHOD FOR CREATING KNOTLESS DOUBLE ROW CONSTRUCT WITH MEDIAL ROW CLOSURE

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 301 days.

(21) Appl. No.: 12/721,974

(22) Filed: Mar. 11, 2010

(65) Prior Publication Data

US 2010/0249834 A1    Sep. 30, 2010

Related U.S. Application Data

(60) Provisional application No. 61/165,330, filed on Mar. 31, 2009.

(51) Int. Cl.
*A61B 17/04* (2006.01)
(52) U.S. Cl. .......................................................... 606/232
(58) Field of Classification Search .................... 606/232
See application file for complete search history.

(56) References Cited

U.S. PATENT DOCUMENTS

| 7,329,272 B2 | 2/2008 | Burkhart et al. |
| 2007/0191849 A1 | 8/2007 | ElAttrache et al. |
| 2009/0318960 A1* | 12/2009 | Burkhart ...................... 606/228 |

* cited by examiner

*Primary Examiner* — Melanie Tyson
(74) *Attorney, Agent, or Firm* — Dickstein Shapiro LLP

(57) ABSTRACT

Systems and methods for soft tissue to bone repairs, without knot tying. The soft tissue repair includes the steps of (i) securing first and second knotless fixation devices in bone, wherein the first fixation device is provided with a first loop and a first set of tails extending therefrom, and wherein the second fixation device is provided with a second loop and a second set of tails extending therefrom; (ii) passing one tail of the first fixation device through the second loop of the second fixation device; (iii) passing one tail of the second fixation device through the first loop of the first fixation device; and (iv) securing the first set of tails with a third fixation device and the second set of tails with a fourth fixation device.

18 Claims, 2 Drawing Sheets

METHOD FOR CREATING KNOTLESS DOUBLE ROW CONSTRUCT WITH MEDIAL ROW CLOSURE

CROSS-REFERENCE TO RELATED APPLICATIONS

This application claims the benefit of U.S. Provisional Application No. 61/165,330, filed Mar. 31, 2009, the entire disclosure of which is incorporated by reference herein.

FIELD OF THE INVENTION

The present invention relates to arthroscopic surgery and, more specifically, to an improved method of attaching tissue to bone, such as rotator cuff repair.

BACKGROUND OF THE INVENTION

Reattachment of soft tissue to bone employing knotless fixation devices are known in the art, particularly for the formation of double row constructs in arthroscopic rotator cuff repairs. For example, the SutureBridge™ tendon repair technique, developed by Arthrex, Inc., and disclosed in U.S. Patent Publication No. 2007/0191849, the disclosure of which is herein incorporated by reference, consists of a tied medial row constructed with two threaded suture anchors, combined with knotless lateral fixation using two Arthrex PushLocks®.

As detailed in U.S. Patent Publication No. 2007/0191849, the construct (shown above) is formed by first preparing two pilot holes for two suture anchors (with suture strands attached) that will be inserted in the medial row. Once the two suture anchors are placed in the pre-formed holes, suture tails from the suture anchors are draped over the tendon and threaded through respective eyelets of two knotless fixation devices (such as Arthrex "PushLock" C anchor, as disclosed and described in U.S. Pat. No. 7,329,272, the disclosure of which is hereby incorporated by reference in its entirety). Two pilot holes are formed (lateral from the two medial pilot holes) to accommodate the two knotless fixation devices with the suture tails threaded therethrough. A driver (with a screw inserted on a rod of the driver) is advanced to the edge of each pilot hole and used to install each knotless fixation device (and the corresponding screw) within the pilot hole to form the final construct (shown above) having an exemplary criss-cross suturing configuration. The construct enhances footprint compression and promotes tendon healing-to-bone with decreased knot tying.

The SpeedBridge™ technique, also developed by Arthrex, Inc., uses a threaded swivel anchor (such as disclosed in U.S. Patent Publication No. 2008/0004659, the disclosure of which is herein incorporated by reference) combined with FiberTape® (disclosed in U.S. Patent Publication No. 2005/0192631), the disclosure of which is herein incorporated by reference) to create a quick and secure SutureBridge construct with no knots and only two suture passing steps.

In the SpeedBridge™ technique, a swivel anchor, preferably an Arthrex 4.75 mm SwiveLock® C, loaded with one strand of FiberTape®, is inserted into a medial bone socket. A FiberLink™ and Scorpion™ is used to shuttle both FiberTape® tails through the rotator cuff simultaneously.

Next, one FiberTape® tail from each medial anchor is retrieved and loaded through the SwiveLock® C eyelet. The loaded eyelet is inserted into a prepared lateral bone socket until the anchor body contacts bone, and the tension is adjusted if necessary.

The SwiveLock® C driver is rotated in a clockwise direction to complete the insertion. Using an open ended FiberWire®® cutter, the FiberTape tails are cut, one and a time, to complete the technique.

In the above-described SutureBridge™ and SpeedBridge™ techniques, it can be difficult to tension the sutures or the FiberTape® tails through the rotator cuff, except by deeper insertion of lateral anchors. In addition, the construct formed by the above-mentioned SutureBridge™ technique still requires the formation of knots on the medial row for completing the construct. Accordingly, a double row construct with a knotless medial row and increased tensioning (without deeper insertion of the lateral anchors) is needed.

SUMMARY OF THE INVENTION

The present invention provides systems and methods of forming a knotless double row construct with medial row closure. Loops are created by the placement of medial anchors. One tail from each of the medial anchors is passed through the loop of an adjacent medial anchor, and then the passed tail is secured to a corresponding lateral anchor. In this manner, a completely knotless construct, with a crossing pattern and increased tensioning, is obtained. The knotless repair with medial row closure of the present invention also prevents fluid leakage.

These and other features and advantages of the present invention will become apparent from the following description of the invention that is provided in connection with the accompanying drawings and illustrated embodiments of the invention.

DETAILED DESCRIPTION OF THE INVENTION

The present invention provides systems and methods of forming a knotless double row construct with medial row closure. Loops are created by the placement of medial anchors. One tail from each of the medial anchors is passed through the loop of an adjacent medial anchor, and then the passed tail is secured to a corresponding lateral anchor. In this manner, a completely knotless construct, with a crossing pattern and increased tensioning, is obtained. The knotless repair with medial row closure of the present invention also prevents fluid leakage.

The present invention also provides a completely knotless, double-row construct with a crossing pattern and increased tensioning. A method of soft tissue fixation of the present invention comprises inter alia the steps of: (i) providing a plurality of medial anchors, at least one of the plurality of medial anchors being preloaded with a flexible member (such as suture or tape) attached to the medial anchor, the flexible member forming a loop and two free limbs when the anchor is placed within tissue; (ii) fixating the plurality of medial anchors within a first plurality of bone sockets; (iii) passing through the loop of the medial anchor a flexible member attached to an adjacent medial anchor; (iv) providing a second plurality of bone sockets; and (v) securing the flexible member (passed through the loop) within one of the second plurality of bone sockets.

The present invention also provides a method of knotless fixation of soft tissue by inter alia (i) securing first and second knotless fixation devices in bone, wherein the first fixation device is provided with a first loop and a first set of tails extending therefrom, and wherein the second fixation device is provided with a second loop and a second set of tails extending therefrom; (ii) passing one tail of the first fixation device through the second loop of the second fixation device; (iii) passing one tail of the second fixation device through the first loop of the first fixation device; and (iv) securing the first set of tails with a third fixation device, and the second set of tails with a fourth fixation device.

The present invention also provides a suture construct comprising (i) a first knotless fixation device with a first suture loop and a first set of suture legs, the first suture loop and the first set of suture legs being securely attached to a body of the fixation device; and (ii) a second knotless fixation device with a second suture loop and a second set of suture legs, the second suture loop and the second set of suture legs being securely attached to a body of the fixation device; wherein one suture leg of the first fixation device is passed though the second suture loop of the second device, and wherein one suture leg of the second fixation device is passed though the first loop of the first device.

Figure 1:
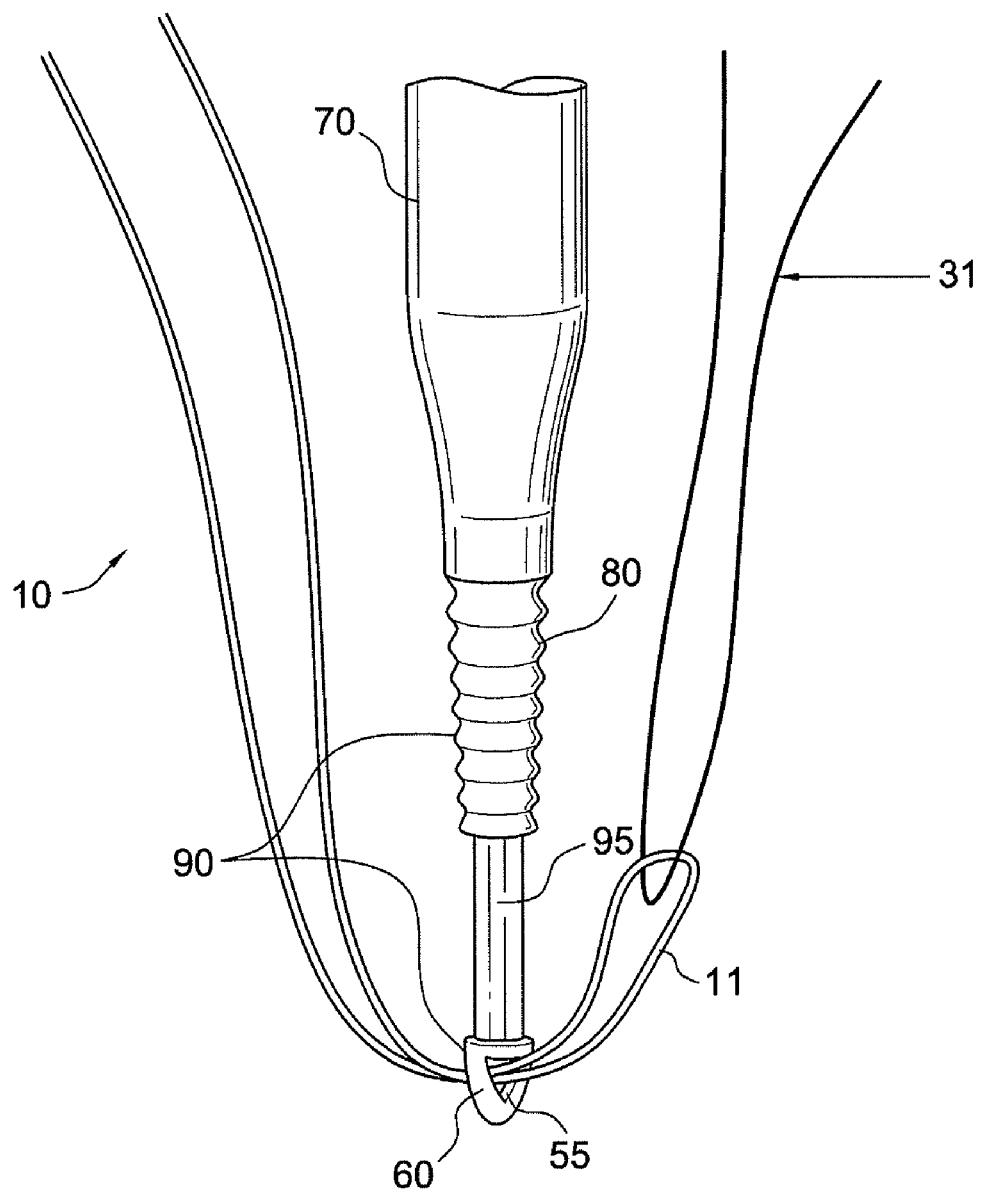
FIG. 1 illustrates a length of flexible strand (such as suture tape or suture strand) positioned on a driver and threaded through a knotless anchor (SwiveLock C anchor) to form a loop, and according to an exemplary embodiment of the present invention.
Figure 2:
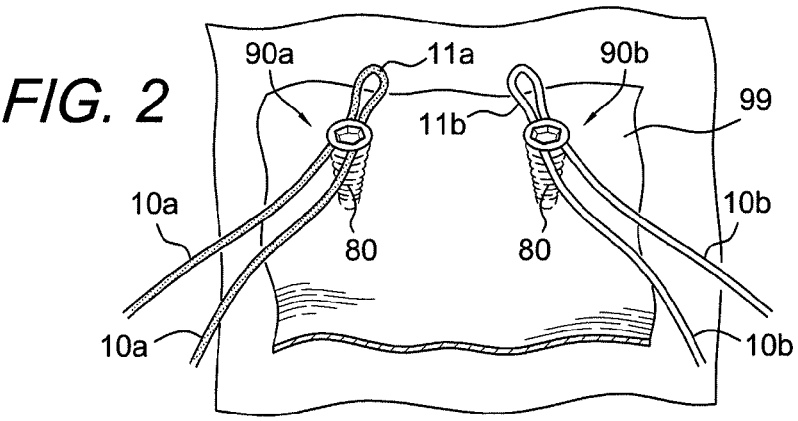
FIGS. 2-4 illustrate an exemplary soft tissue repair with the loop of the flexible strand of FIG. 1, and according to an exemplary method of the present invention.
Figure 3:
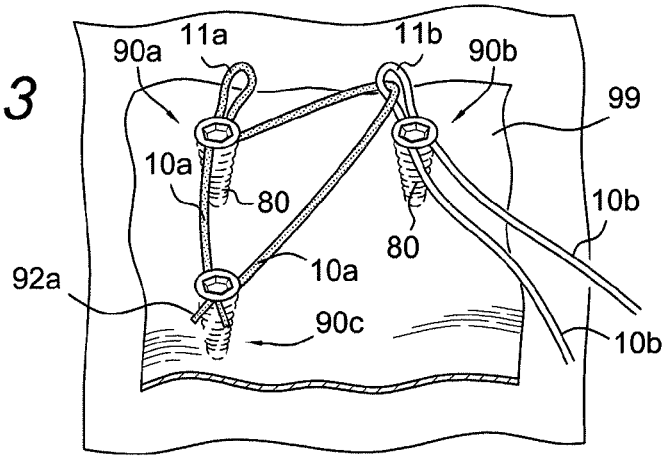
Figure 4:
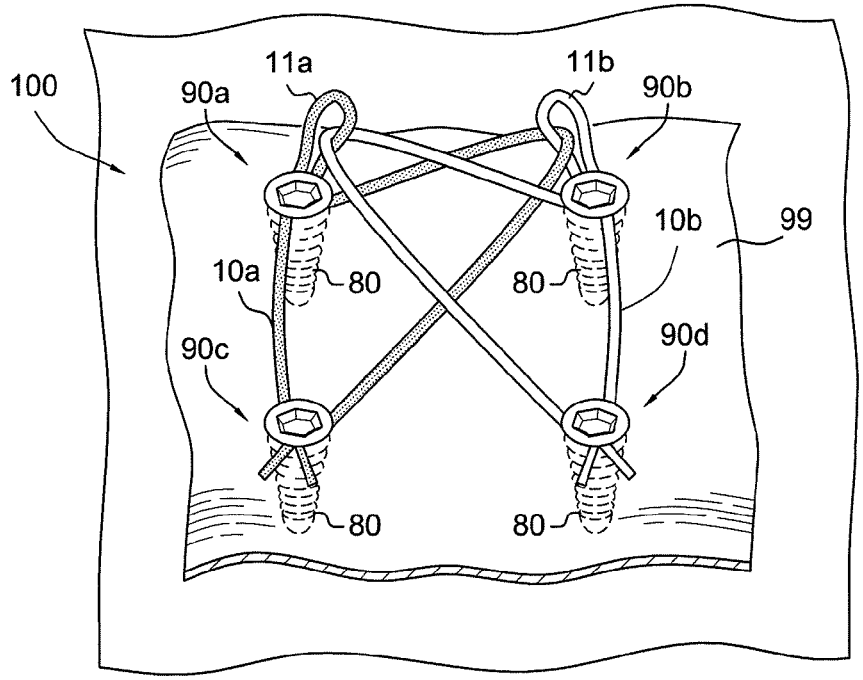

Referring now to the drawings, where like elements are designated by like reference numerals, FIG. 1 illustrates an exemplary embodiment of a length of a flexible strand 10 (suture strand or suture tape 10) passed through an eyelet of a knotless fixation device and forming a loop 11. FIGS. 2-4 illustrate exemplary steps of a method of forming a double row construct 100 with the loop 11 of the suture or tape of FIG. 1.

As illustrated in FIG. 1, flexible strand (suture strand or suture tape) 10 is threaded through an eyelet 55 of a knotless fixation device 90 such as an Arthrex SwiveLock® C anchor (as shown in FIG. 1), and as disclosed and described in U.S. Patent Application Publication No. 2007/0191849, the disclosure of which is hereby incorporated by reference in its entirety. Fixation device 90 may be also an Arthrex PushLock® C anchor (as disclosed and described in U.S. Pat. No. 7,329,272, the disclosure of which is hereby incorporated by reference in its entirety).

The suture strand or tape 10 is threaded through respective eyelet 55 of tip 60 of the fixation device 90 (SwiveLock C anchor 90) to form loop 11. Driver 70 (preloaded with anchor body 80) is advanced to the edge of a pilot hole and used to install the anchor body 80 within the pilot hole. As shown in FIG. 1, loop 11 is positioned on the driver below the anchor body 80 (i.e., about 4 mm prod upon insertion). Anchor body 80 may be a screw, such as a cannulated interference screw, that is inserted over the cannulated shaft of the driver 95 and is advanced so that it is fully seated on the driver tip. Tip 60 is configured to rotate or swivel relative to the driver shaft 95 and anchor body 80. Tip 60 and anchor body 80 may be configured to experience a snap fit when the two pieces forming the SwiveLock® C anchor 90 engage during installation (i.e., when the threaded anchor body 80 is inserted by rotational insertion over the anchor tip 60, to engage the anchor tip 60 and secure the suture anchor in bone).

The suture strand or tape 10 provided with loop 11 of the present invention may be employed for various soft tissue to bone repairs that employ at least one knotless fixation device. According to an exemplary embodiment only, the suture strand or tape 10 is employed in a method of double row fixation of tendon to bone, with medial row closure and with increased tensioning.

FIG. 2 schematically illustrates two medial anchors 90a, 90b with respective flexible strands 10a, 10b forming respective flexible loops 11a, 11b, inserted within tissue (for example, within bone such as humerus for a rotator cuff repair) as described above with reference to FIG. 1. As noted above, the flexible strands 10a, 10b may be suture strands or suture tapes, or combinations thereof. Upon insertion within a pilot hole in the bone, two free limbs or ends of each flexible strand 10a, 10b are attached to each of the medial anchors 90a, 90b, with each of the flexible strands forming loop 11a, 11b, also attached to the respective medial anchor 90a, 90b. As detailed below, the formation of the flexible loops 11a, 11b permits a free limb of one anchor to be passed through a loop of an adjacent anchor and to improve the fixation, stability and tensioning of the soft tissue repair.

FIG. 3 illustrates the construct of FIG. 2 with one of the two limbs of flexible strand 10a passed through loop 11b of adjacent medial anchor 90b. The two limbs of flexible strand 10a are then retrieved from the medial anchor 90a (including the limb passed through loop 11b of medial anchor 90b) and then preloaded through an eyelet of a third fixation device 90c (for example, a knotless fixation device such as a SwiveLock C anchor 90c). Once a lateral bone socket is prepared, the two limbs of flexible strand 10a and the third fixation device 90c (lateral anchor 90c) are inserted within the prepared lateral socket (employing driver 70 of FIG. 1, for example). Once the body of anchor 90c is in contact with the bone, the driver is rotated in a clockwise direction to insert the anchor body until it is flush with the bone.

FIG. 4 illustrates the construct of FIG. 3 with one of the limbs of flexible strand 10b passed through loop 11a of adjacent medial anchor 90a. The two limbs of flexible strand 10b are then retrieved from the medial anchor 90b (including the limb passed through loop 11a of medial anchor 90a) and then preloaded through an eyelet of a fourth fixation device 90d (for example, a knotless fixation device such as a SwiveLock C anchor 90d). Once a lateral bone socket is prepared, the two limbs of flexible strand 10b and the fourth fixation device 90d (lateral anchor 90d) are inserted within the prepared lateral socket (employing driver 70 of FIG. 1, for example). Once the body of anchor 90d is in contact with the bone, the driver is rotated in a clockwise direction to insert the anchor body until it is flush with the bone. In this manner, a final construct 100 (FIG. 4) is obtained, with a crossing pattern wherein medial loops 11a, 11b of the medial anchors allow increased tensioning of the flexible strands 10a, 10b and the formation of the knotless device.

The flexible strand 10, 10a, 10b of the present invention may contain a high strength suture material with surgically-useful qualities, including knot tie down characteristics and handling, such as Arthrex FiberWire® suture disclosed in U.S. Pat. No. 6,716,234, the disclosure of which is incorporated herein by reference. The sutures may be provided with optional colored strands to assist surgeons in distinguishing between suture lengths with the trace and suture lengths without the trace.

The flexible strand 10, 10a, 10b of the present invention may be also provided in the form of a suture tape (such as the FiberTape® disclosed in U.S. Patent Publication No. 2005/0192631, the disclosure of which is herein incorporated by reference), or a combination of suture strand and suture tape.

Preferably, the strands 10, 10a, 10b (including loops 11, 11a, 11b) are provided as color contrasting strands to assist surgeons in distinguishing between them while passing one limb of each strand through the loop of the other strand, as described above. For example, strands 10, 10a, 10b may be provided with tinted tracing strands, or otherwise contrast visually with the other regions of the suture (which remains a plain, solid color, or displays a different tracing pattern, for example). Accordingly, when the suture strand or tape is loaded through the eyelet of a suture anchor or passed through tissue, for example, at least one of the limbs may be visually coded, making identification and handling of the suture legs simpler.

The double row construct with medial row closure of the present invention may be employed in surgical procedures such as rotator cuff repair, Achilles tendon repair, patellar tendon repair, ACL/PCL reconstruction, hip and shoulder reconstruction procedures, among many others. One benefit afforded by the double row construct with medial row closure of the present invention is that it prevents fluid leakage.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method of fixation of soft tissue, comprising:
    securing a first and a second knotless fixation devices in bone, wherein the first fixation device is provided with a first suture loop and a first set of tails extending therefrom, and wherein the second fixation device is provided with a second suture loop and a second set of tails extending therefrom;
    passing one tail of the first fixation device through the second suture loop;
    passing one tail of the second fixation device through the first suture loop; and
    securing the first set of tails with a third fixation device and the second set of tails with a fourth fixation device.
2. The method of claim 1, further comprising the steps of:
    passing the first and second sets of tails through the soft tissue and over a lateral portion of the soft tissue; and
    anchoring the first and second sets of tails in the bone and laterally from the first and second knotless fixation devices.
3. The method of claim 1, wherein the step of securing the first and second fixation devices in the bone comprises passing a suture strand through an eyelet of each of the first and second fixation devices and inserting each of the first and second fixation devices in the bone to form the first and second suture loops and the first and second set of tails extending from each of the first and second suture loops.
4. The method of claim 1, wherein at least one of the first and second knotless fixation devices is a push-in type anchor.
5. The method of claim 1, wherein at least one of the first and second knotless fixation devices is an anchor with a tip configured to rotate relative to an anchor body.
6. The method of claim 1, wherein at least one of the first and second knotless fixation devices is an anchor with a tip configured to swivel relative to an anchor body.
7. The method of claim 1, wherein the suture loop is formed of suture or suture tape.
8. A knotless method of attaching soft tissue to bone, comprising:
    providing a first medial row constructed with a first plurality of fixation devices, wherein each of the first plurality of fixation devices is a knotless fixation device preloaded with a flexible strand, wherein, upon insertion of each of the fixation devices within bone, the flexible strand forms a flexible loop and two free limbs securely attached to the knotless fixation device;
    providing a second lateral row constructed with a second plurality of fixation devices;
    passing one limb of one of the first plurality of fixation devices through a loop of an adjacent fixation device and then over a lateral portion of the soft tissue, passing one limb of the adjacent fixation device through the loop of one of the first plurality of fixation devices and then over a lateral portion of the soft tissue; and
    securing the two free limbs of each fixation device at an opposite end in a hole in bone by the second plurality of fixation devices.
9. The method of claim 8 further comprising the step of passing the flexible strand through an eyelet of each of the first plurality of fixation devices, and securing the fixation device within a bone socket so that the flexible strand forms the flexible loop and the two free limbs attached to the fixation device.
10. The method of claim 8, wherein the flexible strand is a suture or a tape.
11. The method of claim 8, wherein at least one of the first plurality of fixation devices is a swivel anchor.
12. The method of claim 8, wherein at least one of the first plurality of fixation devices comprises an anchor body and an anchor tip rotatably attached to the anchor body, and wherein the anchor body is configured to be inserted over the anchor tip for securing the suture anchor in bone.
13. The method of claim 12, wherein the anchor body is a cannulated interference screw.
14. A method of fixation o f soft tissue, comprising:
    providing a knotless fixation device having an anchor body and a tip with an eyelet, and a flexible strand passed through the eyelet;
    fixing the knotless fixation device in the bone by inserting the anchor body over the tip so that the flexible strand forms a flexible loop and two limbs attached to the loop, the flexible loop and the two limbs being securely attached to the tip of the knotless fixation device;
    passing a flexible elongated member attached to an adjacent fixation device through the flexible loop; and
    subsequently, passing the flexible elongated member over a lateral portion of the soft tissue, and securing the flexible elongated member with another fixation device.
15. The method of claim 14, further comprising passing the two limbs through tissue and over a lateral portion of the tissue, and securing the two limbs with another fixation device, without tying a knot.
16. The method of claim 14, wherein the tip is configured to rotate relative to the anchor body.
17. The method of claim 14, wherein the tip is configured to swivel relative to the anchor body.
18. A method of tissue fixation comprising:
    providing a first anchor and a second anchor in the proximity of a bone, wherein each of the first and second anchors is preloaded with a length of an elongated flexible member attached to each of the first and second anchors;
    inserting the first and second anchors into first and second bone sockets so that each of the elongated flexible member forms a loop and two attached flexible legs extending from the loop, each loop being securely attached to the corresponding anchor;

passing one leg of the first anchor through the loop of the second anchor, and passing one leg from the second anchor through the loop of the first anchor;

providing a plurality of bone sockets laterally displaced from the first and second bone sockets;

passing the flexible legs of each of the first and second anchors over a portion of a tissue to be fixated; and anchoring the flexible legs into the plurality of bone sockets without tying a knot and using a plurality of fixation devices, thereby providing tissue fixation.

* * * * *